US012714459B2

(12) United States Patent
Niven et al.

(10) Patent No.: US 12,714,459 B2
(45) Date of Patent: Aug. 25, 2026

(54) PATTERN NEEDLES AND CARTRIDGE FOR TATTOO REMOVAL

(71) Applicant: Rejuvatek Medical Inc., Sandy, UT (US)

(72) Inventors: Gregg D. Niven, Kaysville, UT (US); Howard M. Tanner, Wauwatosa, WI (US)

(73) Assignee: Rejuvatek Medical Inc., Sandy, UT (US)

( * ) Notice: Subject to any disclaimer, the term of this patent is extended or adjusted under 35 U.S.C. 154(b) by 31 days.

(21) Appl. No.: 18/436,666

(22) Filed: Feb. 8, 2024

(65) Prior Publication Data

US 2024/0260991 A1 Aug. 8, 2024

Related U.S. Application Data

(60) Provisional application No. 63/534,423, filed on Aug. 24, 2023, provisional application No. 63/522,095, (Continued)

(51) Int. Cl.

| | |
|---|---|
| ***A61B 17/34*** | (2006.01) |
| ***A61B 17/00*** | (2006.01) |
| ***A61B 17/32*** | (2006.01) |

(52) U.S. Cl.
CPC .... *A61B 17/34* (2013.01); *A61B 2017/00769* (2013.01); *A61B 2017/320004* (2013.01)

(58) Field of Classification Search
CPC ........... A61B 2017/00769; A61B 2017/00761; A61B 2017/320004; A61B 17/205;
(Continued)

(56) References Cited

U.S. PATENT DOCUMENTS 2,588,623 A 3/1952 Eliscu
2,840,076 A 6/1958 Noel
(Continued)

FOREIGN PATENT DOCUMENTS

EP 1514574 A2 3/2005
EP 1709989 A1 10/2006
(Continued)

OTHER PUBLICATIONS

"Manual for Dragonfly X2 Tattoo Machine" InkMachines, (May 7, 2010), 33 pages, available at http://www.inkmachines.com/sites/default/files/files/Manual_For_Dragonfly_X2_tattoo_machine_EN_rev1.pdf.

(Continued)

*Primary Examiner* — Brigid K Byrd
(74) *Attorney, Agent, or Firm* — SandBright Intellectual Property; Robert D. Spendlove

(57) ABSTRACT

A disposable cartridge may be used in conjunction with dermal abrasion for tattoo removal. The cartridge may include a needle bundle that is driven in a reciprocating or reciprocating/rotating motion to abrade dermal tissue during the tattoo removal process. The needle bundle may include a plurality of needles arranged in a circular pattern with each needle tangent and abutting the adjacent needle. The needles may be arranged around a central arbor to form a ring of adjacent needles. Alternatively, the needle bundle may include a tubular needle with sharpened tips formed on an end of the tube. A disposable cartridge used in conjunction with dermal abrasion for tattoo removal may also include a seal/spring/retainer combination element that stretches and rebounds to its original shape to provide a spring action and provides a sealing function to reduce or prevent the discharge of a fluid used in the tattoo removal process.

16 Claims, 13 Drawing Sheets

Related U.S. Application Data filed on Jun. 20, 2023, provisional application No. 63/444,183, filed on Feb. 8, 2023.

(58) Field of Classification Search
CPC ........... A61B 17/34; A61B 2017/3454; A61M 37/0076–0084
See application file for complete search history.

(56) References Cited

U.S. PATENT DOCUMENTS 3,672,367 A 6/1972 Scislowicz
3,685,101 A * 8/1972 Egerer .................... D01H 5/14 19/129 R
4,719,825 A 1/1988 Lahaye et al.
4,798,482 A 1/1989 Kruk
4,798,582 A 1/1989 Sarath et al.
4,967,203 A 10/1990 Doan et al.
5,012,797 A 5/1991 Liang et al.
5,833,649 A 11/1998 Atef
5,971,763 A 10/1999 Yau
6,024,706 A * 2/2000 Hsiao ................ A61B 10/0035 600/556
6,206,270 B1 * 3/2001 Huang .................. A45D 44/00 604/47
6,206,502 B1 3/2001 Kato et al.
6,505,530 B2 1/2003 Adler et al.
6,585,694 B1 7/2003 Smith et al.
6,626,865 B1 9/2003 Prisell
6,855,133 B2 2/2005 Svedman
D506,828 S 6/2005 Layne et al.
6,997,923 B2 2/2006 Anderson et al.
7,179,253 B2 2/2007 Graham et al.
7,314,470 B2 1/2008 Malodobry
7,618,429 B2 11/2009 Mulholland
7,905,854 B2 3/2011 Hazut et al.
D651,712 S 1/2012 Gao
8,224,064 B1 7/2012 Hassebrook et al.
D672,460 S 12/2012 Baid
8,663,162 B2 3/2014 Bunting et al.
8,920,379 B2 12/2014 Lee
9,707,384 B2 7/2017 La Fontaine
9,707,385 B1 7/2017 Chen et al.
D793,549 S 8/2017 Defusco
9,750,528 B2 9/2017 Scherkowski
D831,745 S 10/2018 He
10,500,013 B2 12/2019 Turner et al.
D887,001 S 6/2020 Wang
10,702,684 B2 7/2020 Knowlton
D899,594 S 10/2020 Wang
11,020,203 B2 6/2021 Niven et al.
11,040,185 B2 6/2021 Johansson
D931,455 S 9/2021 Wang
D942,008 S 1/2022 Castillo-Garcia
11,529,505 B2 12/2022 Niven et al.
2002/0069726 A1 6/2002 Adler et al.
2002/0193752 A1 12/2002 Lynn
2003/0171767 A1 9/2003 Koplen
2003/0195542 A1 10/2003 Lee
2003/0208167 A1 11/2003 Prausnitz et al.
2004/0116953 A1 * 6/2004 Dixon ............... A61M 37/0076 606/186
2004/0186501 A1 * 9/2004 Su .................... A61M 37/0076 606/185
2005/0010236 A1 1/2005 Frister
2005/0107738 A1 5/2005 Slater et al.
2005/0148567 A1 7/2005 Kjellbotn et al.
2006/0020283 A1 1/2006 Lisec
2006/0258992 A1 11/2006 Stoop
2007/0156095 A1 7/2007 Hazut et al.
2008/0009842 A1 1/2008 Manstein et al.
2008/0033470 A1 2/2008 Kluge et al.
2008/0077170 A1 3/2008 Kluge et al.
2008/0208235 A1 8/2008 Ulmer et al.
2008/0221548 A1 9/2008 Danenberg et al.
2008/0247637 A1 10/2008 Gildenberg
2008/0262416 A1 10/2008 Duan et al.
2008/0287978 A1 11/2008 Hickman
2008/0306502 A1 12/2008 Lisec et al.
2009/0125050 A1 5/2009 Dixon
2009/0151741 A1 6/2009 Ngo
2010/0023003 A1 1/2010 Mulholland
2010/0082019 A1 4/2010 Neev
2010/0121259 A1 5/2010 Lutski et al.
2010/0191268 A1 7/2010 Lee
2012/0041374 A1 2/2012 Lee
2012/0123462 A1 5/2012 Lee
2013/0041266 A1 2/2013 Rockrohr
2013/0123746 A1 5/2013 Bunting et al.
2013/0150878 A1 * 6/2013 Church ................ A61B 17/205 606/189
2015/0202420 A1 7/2015 Miller et al.
2016/0263365 A1 9/2016 Smith
2017/0065362 A1 3/2017 Turner et al.
2017/0065806 A1 3/2017 Niven et al.
2017/0065807 A1 3/2017 Niven et al.
2018/0304048 A1 10/2018 Knutsson
2019/0046777 A1 2/2019 Knowlton
2019/0099199 A1 * 4/2019 Levinson ........... A61B 17/3417
2019/0217072 A1 * 7/2019 Xiao ................. A61M 37/0084
2020/0138467 A1 5/2020 Knowlton
2021/0244496 A1 8/2021 Niven et al.
2021/0330953 A1 * 10/2021 Kortenhorst ........... A61B 90/39

FOREIGN PATENT DOCUMENTS

| | | | |
|---|---|---|---|
| JP | 2003339875 | A | 12/2003 |
| TW | 304872 | B | 5/1997 |
| WO | 1989012440 | A1 | 12/1989 |
| WO | 2005020828 | A1 | 3/2005 |
| WO | 2005027868 | A1 | 3/2005 |
| WO | 2006106062 | A1 | 10/2006 |
| WO | 2008120204 | A1 | 10/2008 |
| WO | 2012099563 | A1 | 7/2012 |

OTHER PUBLICATIONS

Jamielyn Nye, Blue Stencilled Wall, iheartnaptime.net, Sep. 9, 2011.
Tim Van De Vall, Octagon Templates, timvandevall.com, 2014.
International Search Report; International Patent Application No. PCT/US2020/063831; Medline Industries, Inc.; dated Feb. 26, 2021.
How Tatt2Away Works, Tatt2Away—Official Channel, Youtube; Post Date Oct. 9, 2019; Site Seen Feb. 24, 2022; URL: https://www.youtube.com/watch?v=sK14ek90aQ8 (Year 2019).
International Search Report and Written Opinion; International Patent Application No. PCT/US2022/054367; Rejuvatek Medical Inc.; dated Mar. 27, 2023.
Extended European Search Report; European Patent Application No. 23155577.2; Rejuvatek Medical Inc.; dated Mar. 31, 2023.
International Search Report and Written Opinion; International Patent Application No. PCT/US2011/000101; Rejuvatek Medical, LLC; dated Oct. 17, 2011.
Extended European Search Report; European Patent Application No. 20899868.2; Rejuvatek Medical Inc.; dated Apr. 13, 2023.
International Search Report and Written Opinion; International Patent Application No. PCT/US2024/015012; Rejuvatek Medical Inc.; dated Aug. 7, 2024.

* cited by examiner

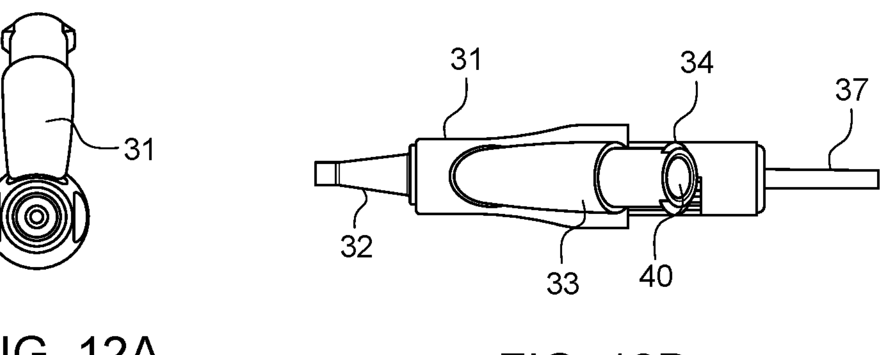
FIG. 12A
FIG. 12B
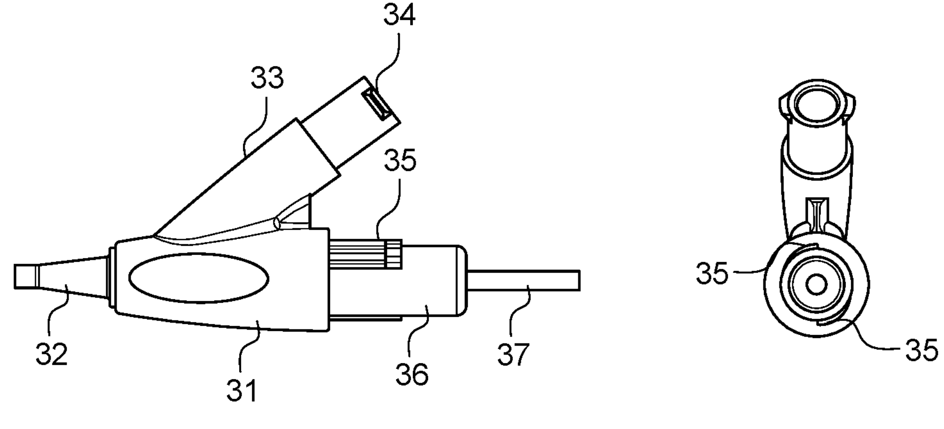
FIG. 12C
FIG. 12D

PATTERN NEEDLES AND CARTRIDGE FOR TATTOO REMOVAL

CROSS-REFERENCE TO RELATED APPLICATIONS

The present application claims priority to the following U.S. Provisional Patent Application No. 63/444,183, filed Feb. 8, 2023; 63/522,095, filed Jun. 20, 2023; and 63/534,423, filed Aug. 24, 2023. Each of which is hereby incorporated by reference.

FIELD OF THE INVENTION

Embodiments of the present invention relate to needles for tattoos and tattoo removal and, in particular, to hollow circular pattern needles or needle sharpened tubes for epidermal abrasion and tattoo removal. Further embodiments of the present invention relate to a cartridge for tattoos and tattoo removal and, in particular, to a cartridge having a combination spring and sealing element.

BACKGROUND

When tattoos are created, tattoo ink is introduced into the epidermis and dermis of the recipient using a group of reciprocating needles coated with ink. The impingement of the needles into the tissue, delivers the desired ink colors via the cavities and groove of the roughened tips of the needles into the tissue dermis layer of the recipient. The ink is then deposited thus, and the ink remains in place throughout the life of the recipient. The inks can be very colorful upon insertion and remain as such for many years. However, as the recipient ages, the colors fade over time, gravitating toward dark blue or black hues. Also, as the age of the recipient advances, the ideas and desires for having obtained a tattoo may be lost or even life changes might require change or removal of the tattoo once thought to be very desirable. Such life changes can be a motivating factor for the desire of the recipient to move toward changing the tattoo shape, wording, colors of the image or even more the recipient to desire the removal.

Many employers including the US military have requirements for tattoo art that doesn't allow visible tattoos. Their requirements only allow such art to be covered when the uniform is worn, or restrictions on the content or coverage of the recipient in obtaining employment or representing the interests of the employer. Others might want to remove their tattoos for reasons other than employment.

In addition, limited studies have been done regarding the chemical nature of some of the inks used in tattoo art, finding that some of these inks can have long term deleterious effects to organs such as the liver. Any ink that is sloughed off within the tissue, can be carried by the lymphatic system to the liver, where it remains for the life of the recipient. Such chemicals can be toxic if allowed to remain. If such is the concern of the recipient, and if additional motives present themselves, it may be advantageous to remove the tattoo by some means in order to alleviate the health concern.

Several methods have been developed for the removal of tattoos, including but not limited to laser impingement of the ink pigments in the skin, dyes or dermal abrasion or bleaching agents. Known methods may include removal of tattoos by abrasion or creating a tegula, however the method to achieve repeatable abrasive methods have been lacking in success, resulting in scarring or discoloration of the replacement tissue generated by the healing nature of the body.

Other known methods may improve the evenness of the abrasion and promote natural healing which would reduce the chance of scarring. One method has been to use the same tools commonly used to apply tattoos. The use of reciprocating tattoo needles may provide an advantage of maintaining an even removal of the epidermis and part of the dermis where the tattoo ink is located. This may include the advantage of a better abrasion or removal of the tissue, but scaring may still occur.

It is also known that if the abrasions are separated by islands, the regrowth of the virgin tissue that surrounds the abrasion allows the scaring to be reduced and the ink removed. A flexible stencil may be used to determine the diameter of the abrasions in a controlled ratio to the skin islands. In this manner, a controlled abrasion would occur that would provide an island of structure that would allow the abrasion to be healed evenly on its circumference. Such islands may allow the healing process naturally in the body to regrow the removed tissue at a controlled rate around the abrasion. Additionally other chemicals liquids may be added to the abrasion to help improve the abrasion process and improve healing.

A process that has received good success in creating the abrasion as well as the healing is the TEPR™ system, a trademark of Rejuvatek Medical Inc. This system uses a stencil that is placed over the tattoo location on the recipient by the clinician. The clinician then marks the pre-defined holes in the stencil using a biocompatible dermatology marker. The clinician then removes the stencil and attaches a needle bundle cartridge to the reciprocating handpiece. The clinician also attaches a fluid control clip to the cartridge and then adds a syringe containing a facilitating fluid such as Teprsol®, a trademark of Rejuvatek Medical Inc., to a line that attaches to the cartridge. The clinician then places the syringe into a pump and fills the line to the cartridge.

Once the line is filled, the clinician energizes the handpiece and places the tip of the cartridge against the tattooed skin, while dousing the abrasion location with Teprsol®. The Teprsol® aids in the abrasion process by softening the tissue being abraded by the reciprocating needles. The clinician then moves the needles around the area marked by the marker, until the epidermis is removed and the dermis containing the ink of the tattoo is exposed. Once the abrasion reveals a smooth surface forming the abrasion, and the ink bed is revealed, the clinician moves their attention to the next treatment site for the abrasion. Once the clinician completes all the treatment sites identified and marked using the stencil, topical ointments and pain reduction mediums are applied. The site is bandaged up to await the scabs to form.

The healing process using the TEPR™ system may be several weeks as scabs or eschars form and the tissue is regenerated underneath. As the scabs dry and slough off, the ink that was revealed during the abrasion is to be found within the scabs. As the scabs are removed, fresh new tissue that was forming underneath the scabs are revealed. After full healing of this treatment area, the clinician will have the recipient return and the clinician will replace a stencil, on the other untreated areas remaining on the tattoo, mark it as before and abrade as was done previously. Using this process, most tattoos can be removed within three treatment cycles without the scaring that had been done prior to this process being developed. Patents and published applications related to this method include U.S. Pat. Nos. 8,663,162; 10,500,013; 10,610,327; 11,020,203; 11,529,505; and D974, 552, and U.S. patent Application Publication Nos. 2020/0108240; 2021/0106398; 2021/0113296; 2021/0244496; 2023/0211138; and 2023/0211139, each of which is incorporated herein by reference.

Other known processes such as bleaching usually only lighten the tattoo and are only successful in lightening the colors. They are usually not as successful in older tattoos, which colors usually bleed and turn darker over time. The laser method may provide some efficacy, but since there is no tissue removal, the tattoo ink is not removed from the body, and can remain in the recipient's body for life. The laser process also has the disadvantage of the pain associated with burning of the cellular structure that retains the tattoo ink. Since lasers work with specific wavelengths of light, only the tissue that absorbs the light quickly and cleanly heats fast enough to boil the fluids in the cells that contain the ink, causing them to release the ink into the circulatory system of the recipient. Once released, the ink-stained ash or debris remaining in the dermis is removed by bodily functions using the circulatory system as with any other dying cellular structures in the body. Since the resultant heating cannot be observed by a clinician, since it is below the epidermis, the clinician may not heat the area enough to remove the ink or heat it too much to cause burns. The resultant burns can be painful and cause scarring as they heal.

Thus, with the TEPR™ abrasive system under the direct observation of the clinician, significant advantages are enjoyed with regard to pain and healing results to the recipient. Since the system is designed that needs these types of needle bundles and cartridges, it is important that the operation of the cartridges and handpiece combination in conjunction with the application of Teprsol® be controlled, simplified as much as possible and designed to prevent unwanted leaks or problems in delivering the resultant abrasion results that are desired for good, repeatable tattoo removal and healing possibilities.

In the removal of tattoos using known abrasive techniques, clinicians employ a specific process of tattoo removal. First, the technician evaluates the tattoo of the client, observing the embedded colors, concentration of color, folds of the skin, wrinkles of the treatment area on the patient and flexibility of the client skin in the tattoo area. After the evaluation, the clinician drapes the areas adjacent to the area to be treated to prevent infection or Teprsol® irritation used during the treatment from affecting other skin areas on the client. The clinician may then apply a topical pain reducing medium to help the client with pain management of the treatment. After the application of the medium, the clinician may adhere a proprietary stencil to the tattooed area that is to be treated, as shown, for example in U.S. Pat. Nos. 8,663,162 and 10,500,013. The clinician then marks the apertures of the stencil, using a biocompatible marker, used for dermatology treatments. After marking the desired apertures of the stencil, the stencil is removed, and the clinician then prepares the abrasion tools necessary for the tattoo removal.

The main tool used in the abrasive treatment is a needle bundle that is mounted in a single use disposable cartridge. Within this cartridge are located on axis with the cartridge, a set of seven solid wire needles. The pattern of these needles consists of one in the center and surrounded by six others tangentially against the center needle, and each needle tangentially against another needle in the group. This group of needles is bundled together and secured to a coaxially attached plastic stem that interfaces with the tattoo removal oscillating handpiece tools. This needle bundle is mounted within the disposable single use cartridge that is installed into a motor driven handpiece.

Embodiments of a needle bundle include those disclosed in U.S. Pat. Nos. 10,610,327 and 11,529,505. The needle bundle stem mentioned previously extends from the proximal end of the cartridge and interfaces with the oscillating driving mechanism in a handpiece the technician uses. The parts within the handpiece contain a motor drive which when powered, creates a reciprocating linear motion of the needle bundle by driving against the end of the stem of the needle bundle. The sharpened tips of the needle bundle which extend from the distal end of the disposable cartridge are then adjusted to a specified distance from the exit aperture of the cartridge.

Once set, the tips of the needles are placed against the tattooed skin of a client. The clinician chooses one of the markings previously made with the marker and uses that and other markings as a guide for the size and spacing of the abrasions that are created for the tattoo removal process. While the needle bundle is being driven with the handpiece, a fluid, such as Teprsol®, is applied to the needles and treatment sites, all while the clinician moves the needle bundle in a circular/spiral motion, starting at the center and spiraling out to the distance of 2.5 mm from the center or the edge of one of the marks made and then doing a rotation around periphery of the mark, then spiraling back to the center.

While this abrasion is occurring, the technician is observing the epidermal tissue removal, fluid liquidity, and consistency of the wound bed being created and for evidence of the ink embedded in the tissue being released. Once satisfied the abrasion is complete, even and the wound is uniform in this location, the clinician wipes the wound with a towel and then selects another mark for the next abrasion. The abrasion process is repeated on each of the marks made until the pattern marked by the clinician is complete. This completes the abrasion process using the seven-needle pattern.

The process of evaluation by the clinician and setup by marking the areas to be treated takes several seconds and possible passes of the needle bundle per location as indicated by the stencil and experience of the clinician. The time required by marking draws out the abrasion process time and for complicated tattoo removals, this process can take from several minutes to one quarter of an hour just for marking. To add to the time of the treatment process, each of the markings destined for treatment, have a specific pattern of abrasion performance that has been developed over time due to the diametral size of the needle bundle being used. Using the known seven needle bundle, the combination of circular and spiral motion of the needle bundle can take up to fifteen seconds per abrasive spot or tegula of possibly more depending upon the resulting tegula creation.

Since a faster time for performing the abrasion could shorten the treatment time and be more conducive to salon profitability and patient comfort, a method that shortens the abrasion time, simplifies the abrasion pattern, and increases the rate of epidermal tissue removal that the technician must perform for each tegula identified using the stencil would be advantageous. If the technician manipulation pattern of the needle bundle could be simplified to fewer or to just one circular pass and still provide even uniform abrasion, this would speed the abrasion process and allow more treatments in a day and help the client deal with less time in dealing the needle impingement on their body. There is, therefore, a need for a different set of needle patterns and stencil pattern creation that may be used which could speed the time of tegula creation, thereby shortening the treatment time.

SUMMARY

Embodiments of the device may be used for the removal of tattoos using abrasion as the method of removal. Embodiments may include a needle bundle located on the central axis of the device consisting of a plurality of needles, tangentially placed against one another in a pattern, attached to a stem that interfaces with a reciprocating handpiece. The tip of the device is placed against the tattoo embedded epidermal tissue to be abraded and the needles are driven in a reciprocating motion by the handpiece into the tissue. During the impingement of the needles, Teprsol® fluid is introduced through the fluid port which is delivered to the abrasion site which helps improve the abrasion process. The cartridge unit containing the needles and interfaces for the Teprsol® delivery and reciprocating needle action is a self-contained device that is closed and fabricated to prevent excess Teprsol® loss to surrounding tissue due to the irritating action of the Teprsol®.

Embodiments of the device are composed of several parts assembled into one assembly. The assembly may comprise a housing encompassing a central axial bore with apertures on each end, and an angle tubular feature protruding from the top of the housing on an angle. This top tubular feature may comprise a hollow bore that extends from the proximal end down to and intersecting with the main axial bore. On the proximal end of this tubular structure a tapered female entrance may be formed, including tabs for locking mating components. This feature may comprise or be referred to as a Luer lock and allow mating parts to create a seal that withstands high pressures yet is easy to remove and change if desired. The use of a Luer lock may have an advantage of eliminating the need to add a fluid control clip.

The distal end of the housing may comprise a mating feature for a tapered tip with a central aperture. This tip holds the needles in the chosen pattern and holds them in place during the abrasion process. The tip is tapered, which may allow the clinician to see just outside of the needle bundle the action of the needles, the condition of the abrasion as it is formed and to monitor the flow of Teprsol® being delivered to the site. The tip and housing can be made in opaque materials, but preferably they are fabricated in translucent or transparent materials. Being fabricated as such they may allow the clinician to monitor flow and to observe any resistance to the flow of Teprsol®.

The proximal end of the housing may comprise two features, 1) a barrel body to which is attached axial ramps that increase in height as the angles change on axis of the part, and 2) an internal bore that extends from the end all the way to the center where there is a wall or barrier that has a central aperture in it. The axial ramps on the barrel may allow the barrel body to be inserted into a reciprocating drive handpiece and twisted on axis until the axial ramps lock within the body of the handpiece. The angles are developed such that they interfere with obround features within the handpiece, thereby locking the barrel and housing into the handpiece at a specified angle every time it is inserted.

In the central bore where the wall or barrier was described, a guide may be inserted. This guide may help keep the needle bundle oriented on axis with the central bore of the housing. This alignment may help keep the needle bundle from rubbing or sliding against the internal walls of the housing. The guide is preferably fabricated from a plastic that has natural lubricity such as nylon, polyethylene or Delrin. These materials may provide a low friction surface for the needle bundle to rid within thereby reducing wear or friction while reciprocating.

A needle bundle may reside on the central axis of the housing. The bundle may comprise a group of 0.3 mm to 0.2 mm diameter needles, tangentially placed against one another in a grouping of seven, nine or thirteen needles. The group of needles may be secured in the stem. The stem of the device is preferably a plastic cylindrical part that has a long cylinder on the proximal end and a small diameter receptacle at the distal end. The distal end contains the non-sharpened end of the needle group installed in the device. The grouping of needles is preferably secured into the small diameter receptacle with an adhesive, lock rings, tubes, or other appropriate mechanisms. Once secured in the receptacle, the needle bundle acts as a single piece assembly.

The distal end or non-aperture end of the stem may interface with the reciprocating drive in the handpiece. By displacing the end of this stem while in the housing, the needle group oscillates in a linear motion. This motion with the sharpened needle tips while impinging on the tattooed epidermis and dermis of the recipient performs the abrasion.

The base of the needles in the bundle may interfaced with a flexible cylindrical shaped part with a hole on the needle side and an larger diameter annulus on the opposing end. The base of the needles may be inserted through the hole in the rubber cylinder and the surface with the small aperture on the stem may be pressed up against the inside of the cylinder. After this insertion, a rigid cylinder retainer ring may be inserted over the end of the needle stem and inserted to a stopping face within the rubber cylinder. After assembly, the needle, stem, and rubber cylinder may be inserted into the proximal bore of the housing, and pressed into the bore until the rubber cylinder annulus stops against the end of the housing thereby forming a stopper.

An advantage of the stopper is that it may form a seal or resistance against possible back flow of Teprsol® toward the handpiece should the tip of the housing become plugged up or clogged. Such a seal may reduce or prevent contamination of the handpiece and reduce or prevent leakage of the Teprsol® which results in reduced corrosion of the handpiece internal components. The seal may perform various functions. It may perform a centering return spring action that helps keep the needle bundle centered and located within the housing. It may act as a seal to reduce the possibility of unwanted Teprsol® backflow, and it also acts as a stopper, which retains the components installed within the housing. It may also bias the needle bundle in a rearward position such that the sharpened tips of the needles or needle tube are retracted within the distal end of the housing in a manner that prevents or reduces puncture injury to the clinician during installation and after removal of the cartridge.

Among other advantages of embodiments of the invention, being larger diameter than known tattoo needle bundles, the circular pattern needles abrade more of the epidermis and dermis in a rate that is faster than the traditional needle patterns used due to the diameter covered. The diameter of the circular pattern or tube can be up to half of the planned abrasion site and can be manipulated by a clinician in a simple circular motion rather than the longer spiral patterns traditionally used for dermal abrasion and small needle bundles. Embodiments as discussed herein may include needle patterns, use, and construction methods.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings.

FIG. 12A is a front orthographic view of a cartridge in accordance with embodiments of the device of FIG. 10.

FIG. 12B is a top orthographic view of a cartridge in accordance with embodiments of the device of FIG. 10.

FIG. 12C is a side orthographic view of a cartridge in accordance with embodiments of the device of FIG. 10.

FIG. 12D is a rear orthographic view of a cartridge in accordance with embodiments of the device of FIG. 10.

DETAILED DESCRIPTION

Figure 1:
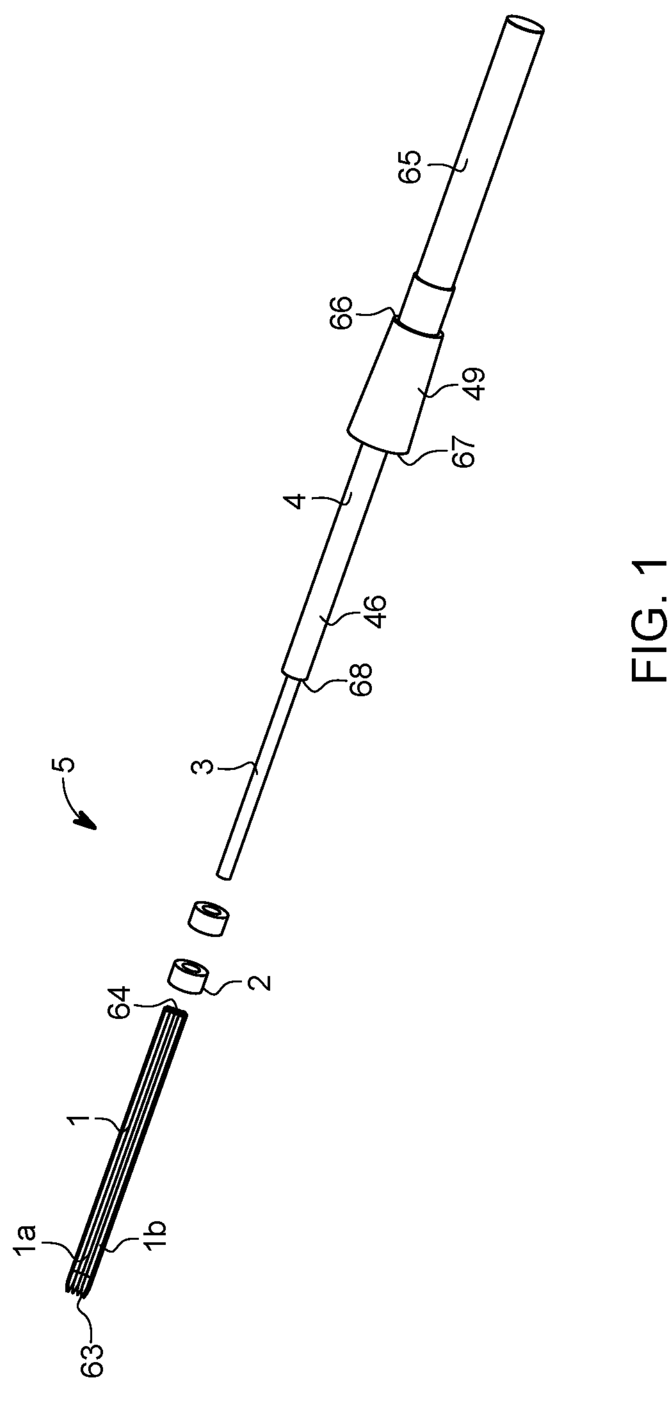
FIG. 1 is an exploded perspective view of an illustrative embodiment of a needle bundle assembly.

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, forward and rearward, and the like may be used solely to distinguish one entity or action from another entity or action without necessarily requiring or implying any actual such relationship, direction or order between such entities or actions.

The terms "proximal" and "distal" are used throughout this application when describing various embodiments. These terms are not intended to be limiting and are merely provided for ease of maintaining a consistent orientation when describing various embodiments. As used herein, proximal refers to the direction generally closer to a user of the cartridge and distal refers to the direction generally farther from the user.

The term Teprsol® is used throughout this application when describing a facilitating fluid that aids in various embodiments of the abrasion and removal of tattoos or other skin markings. It will be understood by one of ordinary skill in the art that the facilitating fluid may be Teprsol®, a trademark of Rejuvatek Medical Inc. Alternatively, the facilitating fluid may be another appropriate fluid as would be understood by one of ordinary skill in the art.

Embodiments of the inventive device may comprise a of patterns of circular sharpened needles or sharpened points on hypodermic tubes that can be used to abrade the epidermis. This arrangement of needles or sharpened tips on the tubes create a hollow circular pattern and omits a central needle that is present on other smaller circular patterns such as a known pattern of seven round, adjacent needles. Embodiments of the ring pattern of needles may comprise sharpened needles that are placed tangentially against one another in a circular pattern. The circular hollow pattern that is created with such a tangential arrangement is maintained either by pressure of the needles against one another within a constraining tube, and/or by the needles being placed against an arbor or central pin whose diameter is such that the needles maintain a tangential relationship between the arbor and each needle in the arrangement and then constricted in that position by a constraining tube or retainer. The central arbor, if large enough in diameter, could be part of the molded stem that is used to drive the needle bundle in a linear oscillating motion when placed within a holder such as a cartridge housing, and then driven by a handpiece that is set up to accept the stem and housing and drive the needles attached.

Embodiments of the arrangement of needles or sharpened tube points may comprise of any number of needles arranged in a ring pattern or any number of sharpened points on the end of the tube. Due to the small diameters that usually accompany hypodermic tubing and the final size of the tegula created the diameters of the tubing preferably would not exceed half of the diameter of the final tegula, that being about 2.5 mm in diameter. Due to the small diameter of the tubing, an even quantity of points may be created, to allow a cutter, such as a wire EDM machine to cut the tips. This would allow tips on opposing sides of the tubing to be created with the tapered cuts. Such cutting of the tube could also be done with a laser cutter.

An additional benefit of the circular tubing bundle is that Teprsol®, which is used to aid in the abrasion process, could enter the side of the tubing through radially placed slots to help in the abrasion process in addition to that which would be able to be delivered to the treatment site that may be emitted around the circumference of the tube, near the tip of the plastic housing. The additional flow of Teprsol® may allow the abrasion process to occur more easily and help to prevent fluid blockage that abraded tissue creates in needle bundles that occurs when needles are tangentially arranged as in a seven-round pattern.

When needles are used in embodiments of a ring arrangement, from seven up to twenty-two needles may be used in creating a circular pattern. The needles may be hollow or solid wire needles. The needles may preferably have a diameter between 0.2 and 0.5 mm and more preferably a diameter of 0.3 mm. Alternatively, the needles may have other diameters, shapes, or configurations as set forth herein or as would be understood by a person having ordinary skill in the art. An arrangement of twenty-two needles in a circular pattern would allow the clinician to abrade just over half of a 5 mm diameter tegula. The pattern of motion that the clinician performs might be simplified to only a circular motion for large patterns of twenty-two needles, providing that the oscillation of the needles is consistent with the an application using approximately 8000 punctures per min. The simplified motion and larger area of abrasion can offer the clinician a way to simplify the needle manipulations and speed the abrasion process by removing more tissue due to the larger diameter of the needle group when compared to a known needle bundle.

Needle bundles constructed in accordance with embodiments of the present invention, including with a central arbor to which needles are placed tangentially against the side of the arbor can be fabricated in many ways. Examples shown in the figures may include an assembly with needles placed against a molded plastic stem, the arbor of which is extended to and controls where the needles will be placed. The needles are then arranged with the tips pointing away from the proximal end of the stem and placed tangentially against the arbor and secured with a metal shrink ring.

Alternatively, a separate wire arbor that may be inserted into a tubing sleeve sized to securely hold a predetermined quantity of needles and arbor, and then surrounded by needles to fill in the pattern. The needles extend from the distal end of the tubing and the tubing may be secured to the proximal end of the needles by an adhesive, or by a special crimping tool. After the crimping or securing of the needles to the arbor and the tubing, the needle bundle can then be inserted into and secured by an adhesive to a stem that has a mating hole receptacle that can accept the needle bundle. Such embodiments would allow the tubing and arbor to be varied in length to add flexibility to the needles by a shorter tube and arbor or to restrict the flexibility of the needles by increasing the length of the tubing and arbor. This variation allows the needle splay and flexibility to be more controlled during manufacture and for the needle bundle to be tailored to the abrasion application.

Embodiments of the abrasion devices may use a disposable plastic housing that is a plastic molded part that has a retaining feature on the proximal end and an aperture from which the needles can protrude during oscillation on the distal end.

Embodiments of a ring needle design comprise needles, an arbor stem combination, and a securing ring or tube that holds the needles tangentially to each other and to the central arbor stem. The needle arrangement may comprise different numbers of needles, including seven needles up to twenty-five needles, and more preferably nine needles up to twenty-two needles. The upper limit being that the diameter of the needle bundle will be up to half of the diameter of the proposed abrasion site. Larger than that diameter, the tegula created does not heal as well and the extra motion adds nothing to the final abrasion result.

In accordance with embodiments of the invention, when placed within the cartridge housing, and attached to a drive handpiece, the needle bundle is oscillated which when placed against the epidermis containing the tattoo, along with Teprsol® fluid being applied to the treatment site, abrasion of the epidermis containing the tattoo ink is performed.

FIG. 1 displays the various parts of a circular needle bundle 5 and accompanying stem 4 disassembled in an exploded format. Consistent with the discussion above, embodiments may comprise a plurality of needles 1. The plurality of needles may comprise individual needles 1*a*, 1*b* tangentially arranged. The needles 1 may be positioned such that the outside surface of one needle abuts the adjacent need. Each needle may have a pointed distal end 63 and a proximal end 64. One or more securing rings 2 may surround the plurality of needles to secure the needles against an arbor or central pin 3 such that the needles reciprocate and/or rotate in conjunction with the central pin. The pin 3 may extend from or form part of a stem 4 to which the needles are attached.

The stem 4 provides the driving rod 65 that interfaces with a handpiece containing a reciprocating drive. The stem 4 may also comprise a stepped section 49 that provides a connection with between a stem distal portion 46 and the driving rod 65. The stepped section 49 may have a larger diameter then the stem distal portion 46 and driving rod 65, and the diameter may increase and decrease in one or more steps 66, 67. The central pin 3 may extend from a distal surface 68 of the stem distal portion 46. The proximal end 64 of the needles may about the distal surface 68 of the stem. Alternatively, the proximal end 64 of the needles may be inserted into one or more cavities formed in the distal surface 68 or may be embedded in the stem 4 at the distal surface 68. The stem 4 may be molded or machined from a plastic material or other appropriate material.

Figure 2:
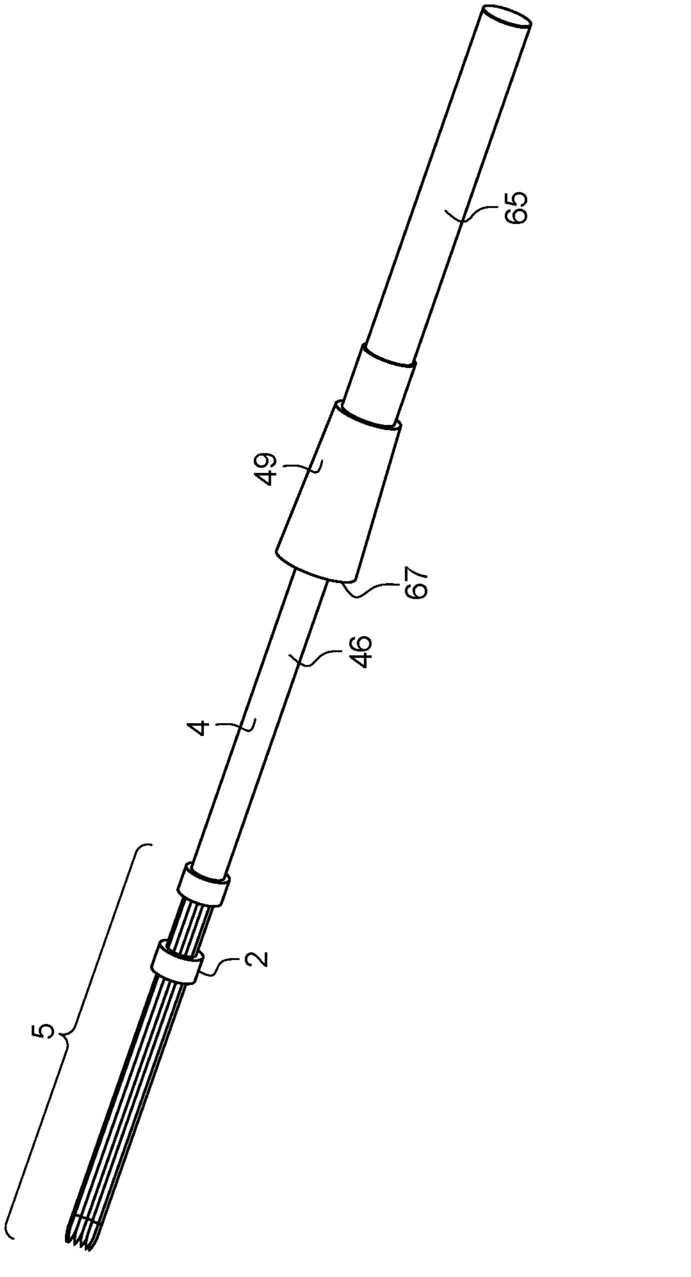
FIG. 2 is a perspective view of the needle bundle assembly of FIG. 1 as assembled.

FIG. 2 shows the needle bundle 5 assembled and secured to the stem 4. Once assembled, the needle bundle can be inserted into a cartridge housing for use in the abrasion process.

Figure 3:
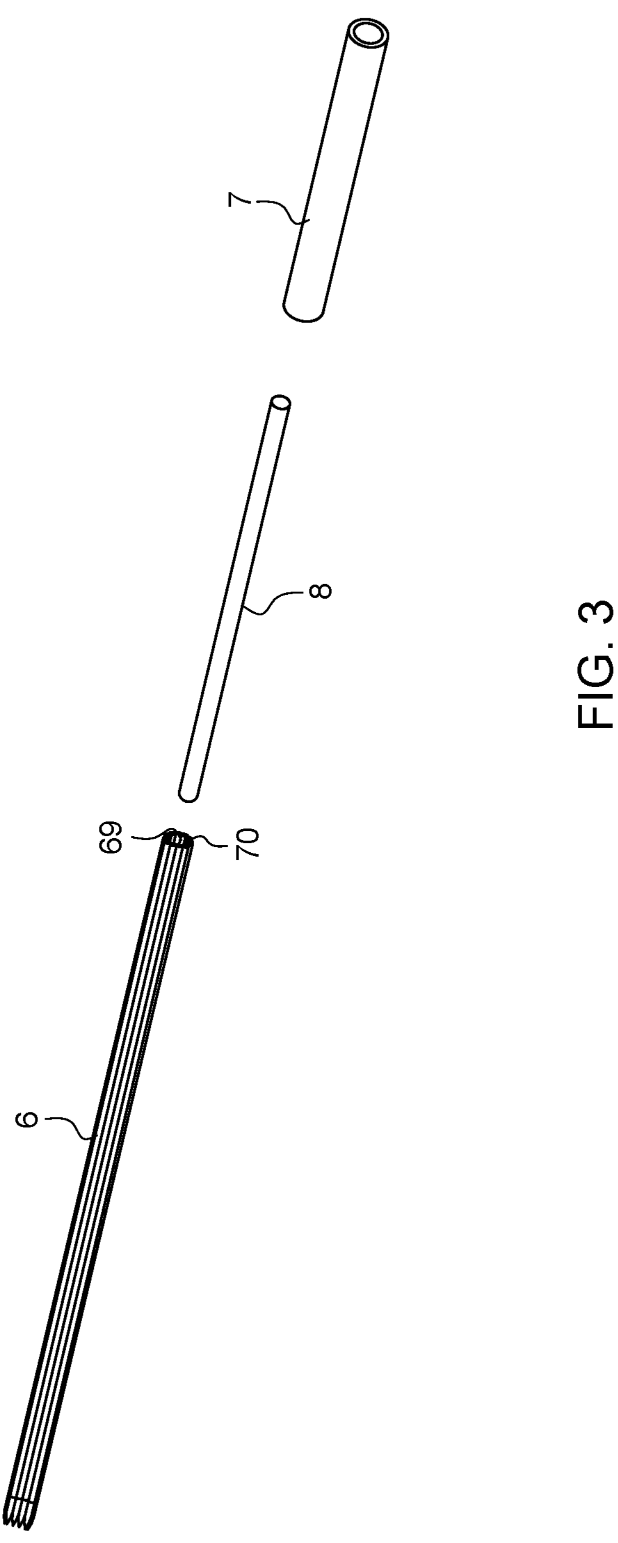
FIG. 3 is an exploded perspective view of components of a further illustrative embodiment of a needle bundle assembly.

FIG. 3 illustrates an alternative embodiment that may employ an alternative method of construction. In such embodiments, the needles 6 may be inserted into a tube 7, and a central wire arbor 8 installed into a central void 69 forcing the needles against the inside wall of the tubing such that the needles form a ring 70 surrounding the central void 69. The central wire arbor 8 may have an interference fit within the ring of needles such that the arbor holds the needles against and inner surface of the tube 7 and secures the needles against movement relative to the arbor. The arbor 8 may be formed from metal wire, plastic, or another appropriate material.

Figure 4:
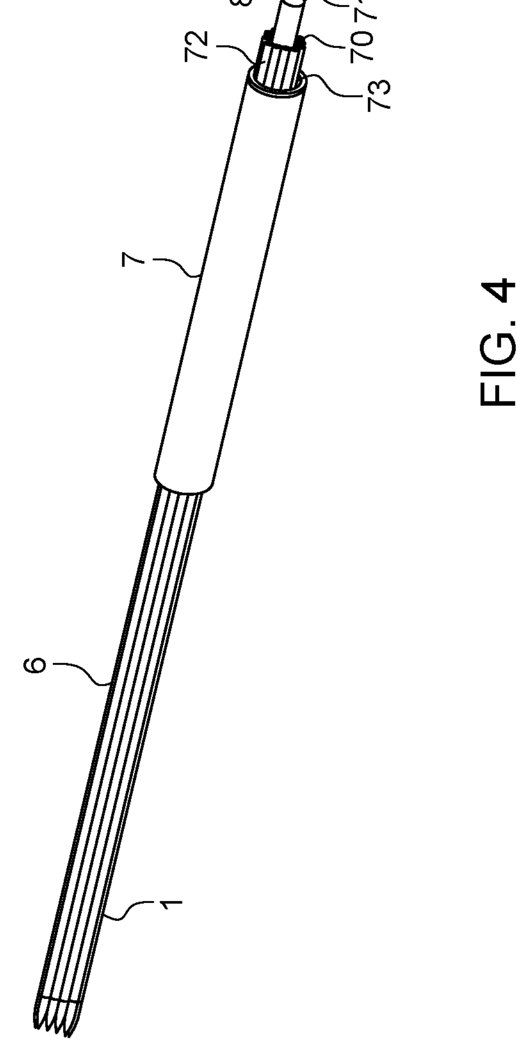
FIG. 4 is a perspective view of the needle bundle assembly of FIG. 3 as assembled.
Figure 5:
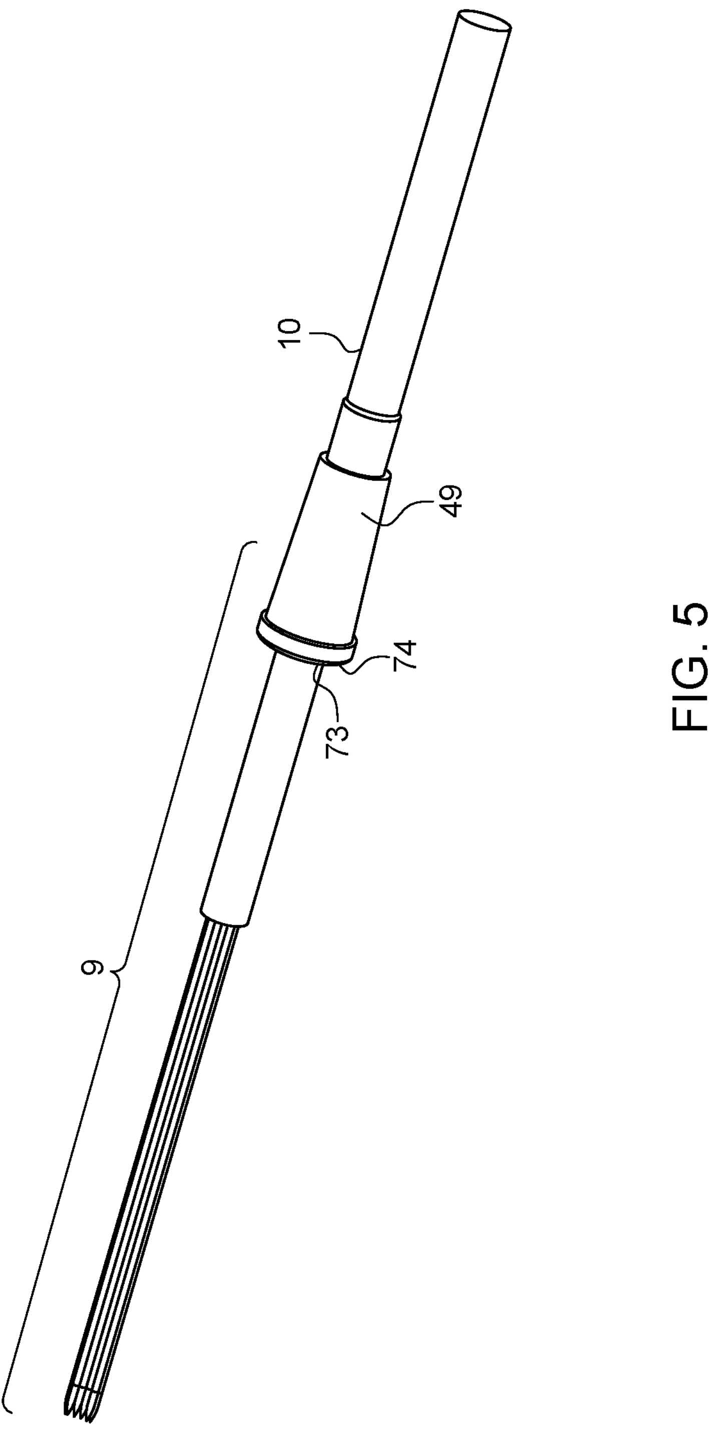
FIG. 5 is perspective view of a further illustrative embodiment of a needle bundle assembly.

FIG. 4 shows the assembly of FIG. 3 completed and secured. A proximal section 71 of the arbor may extend beyond the needle proximal ends 64. This proximal section 71 may provide a location for attachment to a stem 10 (FIG. 5). The tube may be spaced a distance 72 from the proximal ends 64 of the needles 1.

FIG. 5 illustrates embodiments of a needle assembly 9 attached to a molded or machined stem 10 that, when placed within a housing, can interface with the reciprocating drive mechanism in a handpiece. The completed bundle 9 may be secured into the stem 10 with an adhesive. Alternatively, the central arbor 8 may be integrally formed with the stem 10 or attached to the stem by welding, chemical or physical bonding, or by press fit. In the assembled position, a proximal end 73 of the tube 7 may abut a distal surface 74 of the stem stepped portion 49.

Figure 6:
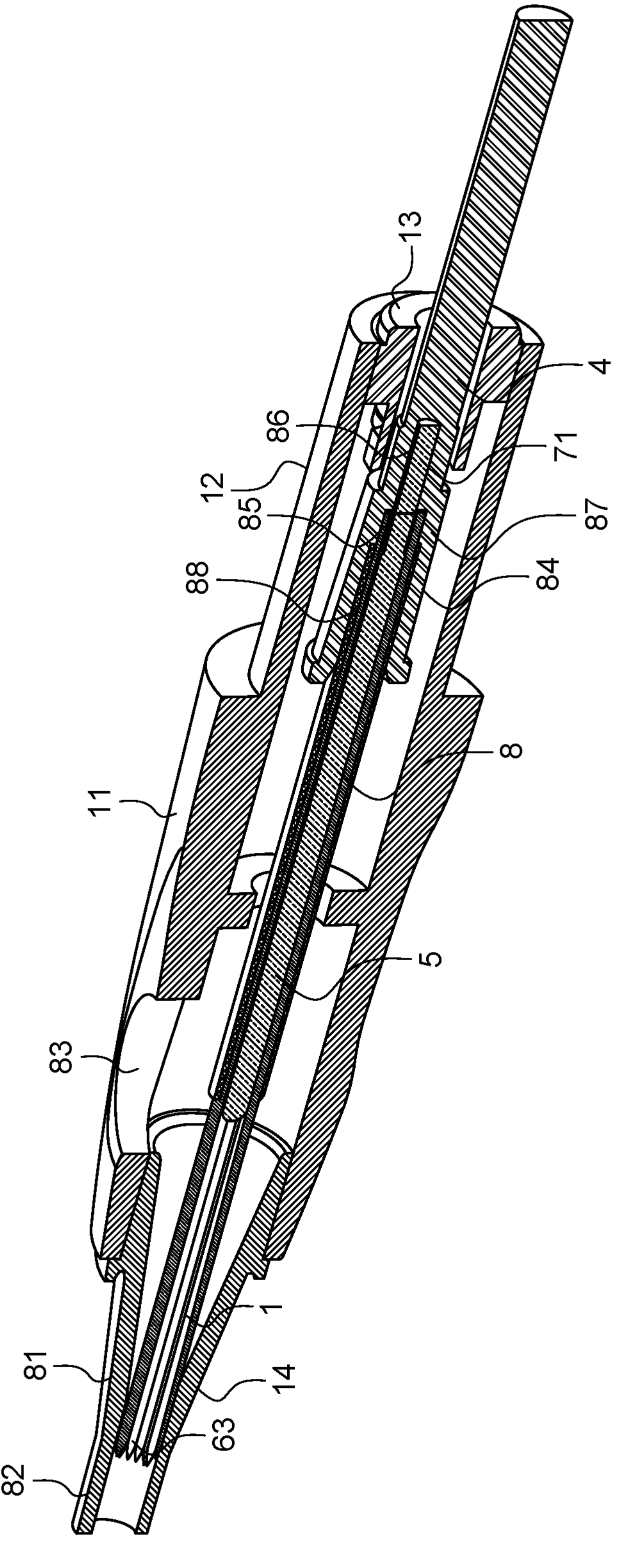
FIG. 6 is a cut-away perspective view of an illustrative needle bundle assembly assembled into a housing.

FIG. 6 illustrates an embodiment incorporating the needle assemblies shown in FIGS. 1 through 5 assembled into a housing 11 that can be inserted into a handpiece for abrasion. The housing 11 may comprise a feature or surface 12 to be used in securing the housing into the handpiece and a way to center the needle bundle for axial control during reciprocation. Centering may be provided by a bearing surface 13 on the proximal end and a tapered conical tip 14 on the distal end. The housing 11 may comprise a conical distal section 81 through which the sharpened tips 15 or pointed ends 63 of needles 1 extend. The distal section 81 may comprise a generally cylindrical end portion 82 that extends from the distal end of the conical section 81. As shown in FIG. 6, the needle ends 63 may be retracted within the end portion 82 when the needle bundle 5 is in a retracted position.

The surface 12 may comprise a cylindrical body that is inserted into and secured to a handpiece (not shown). The housing may have various features as discussed below with regard to FIGS. 9-13, including a passageway 83 through which Teprsol® may flow into the housing. The stem 4 may comprise a distal section 84 having a bore 85 formed therein to accommodate a proximal end of the needle bundle 5. The bore may have stepped portions to encompass the proximal section 71 of the arbor 8 that extends beyond the proximal end of the needles 1 in a first section 86, the ring of needles 70 in a second section 87, and the sleeve 7 in a third section 88.

One aspect of embodiments illustrated in FIGS. 4 and 5, is that the tubing 7 that supports the needle bundle 9 can be made shorter or longer, depending upon the need for more flexible needles. FIG. 1 illustrates embodiments that comprises needles 1 that are approximately ½ the length of the needles 6 in FIGS. 4 and 5. The embodiment of FIG. 1 would result in very stiff needles dependent upon the diameter and modulus of the material the needles are constructed from. Lengthening the needles would result in a more flexible needle.

With reference to FIGS. 3 and 4, varying the length of the tube 7 and arbor 8 in the assembly may allow the needle bundle to be made by one skilled in the art to have a specific bundle or a range of bundle flexibilities that can be tailored to various skin types. Since some clinicians prefer more flexible needles, they may feel the result is a more uniform abrasion. Conversely, needle bundles with a longer tube 7 and arbor pin 8, may have less flexibility of the needles during oscillation. The change in length may vary the stiffness and flexibility of the needle bundle.

Figure 7:
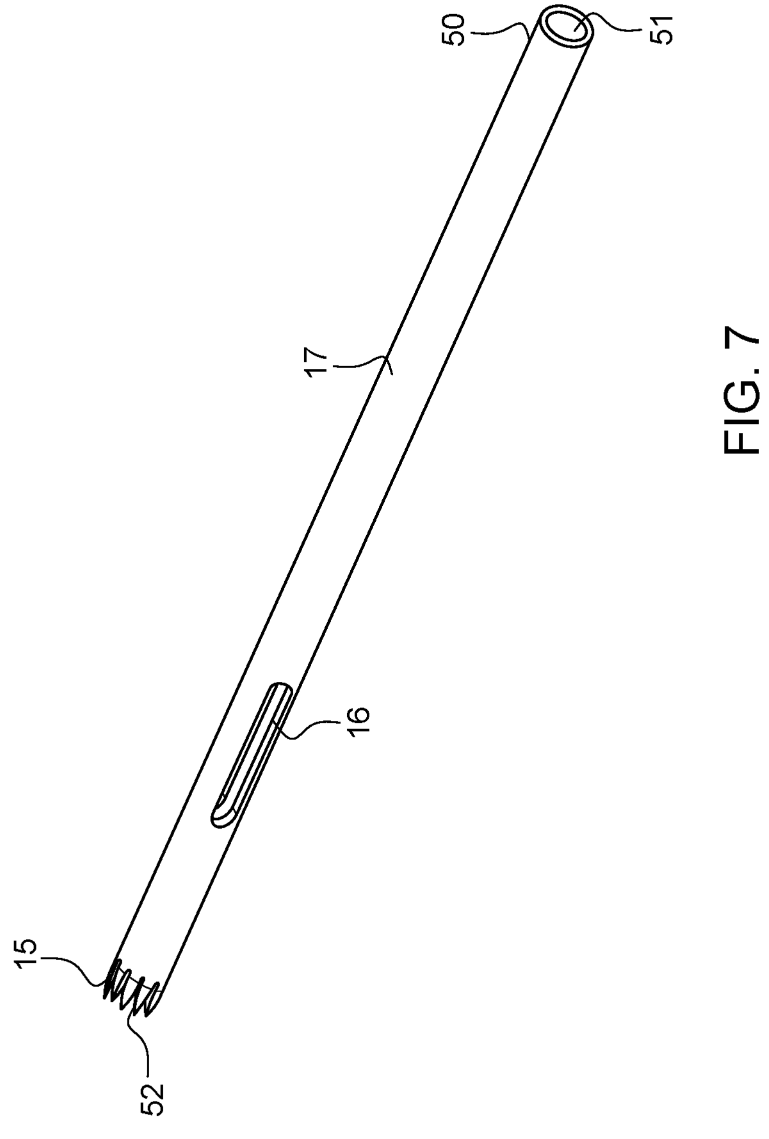
FIG. 7 is a perspective view of an illustrative embodiment of a needle tubing.
Figure 8:
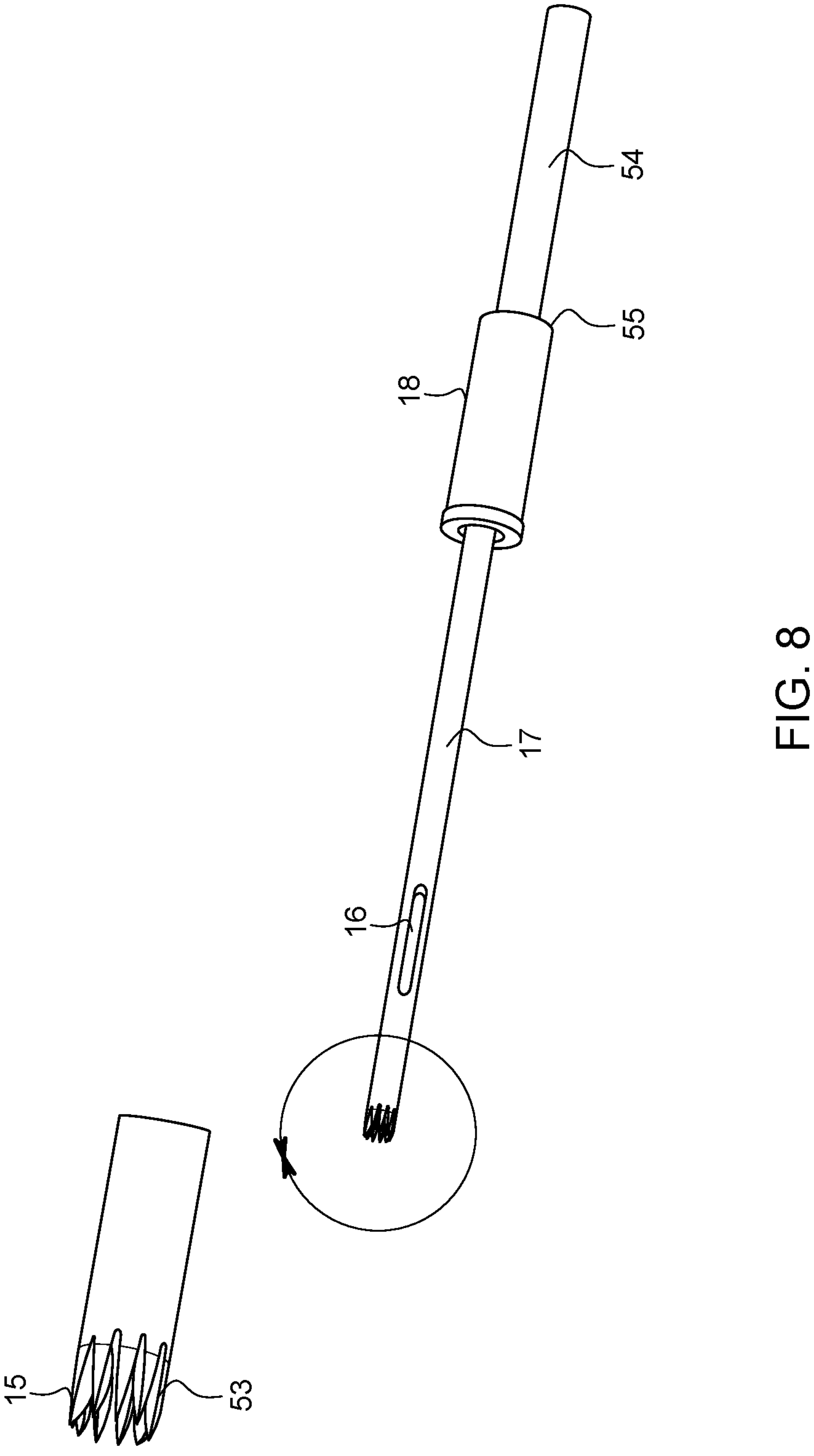
FIG. 8 is a perspective view of an illustrative needle tubing assembled to a stem, including a detail view of the tips.

FIG. 7 shows embodiments of a needle tube 17 used for abrasion. The needle tube 17 may comprise a hollow body having open proximal 51 and distal 52 ends and a circular sidewall 50 and a plurality of sharpened tips 15 formed on a distal end of the circular sidewall. The tips 15 may be sharpened both inside the tube and outside and then cut to a pattern such as the illustrated pattern using a common cutting method for miniature machining. The tips may be formed by cutting grooves 53 or serrations into the sharped end of the tube to form a plurality of tips. The grooves may comprise a single angle or may comprise sections having different angles to create a variable profile tip. The slot 16 apertures on the side of the tube allow the Teprsol® fluid to enter the tubing during an abrasion procedure and help clear tissue from accumulating on the needle or within. FIG. 8 shows embodiments of the tubing needle 17 attached to the stem 18, including a detail view of the tips 15. The stem my comprise a driving rod 54 extending from a distal end 55 of the stem 18. The driving rod may interface with a handpiece containing a reciprocating drive.

Figure 9:
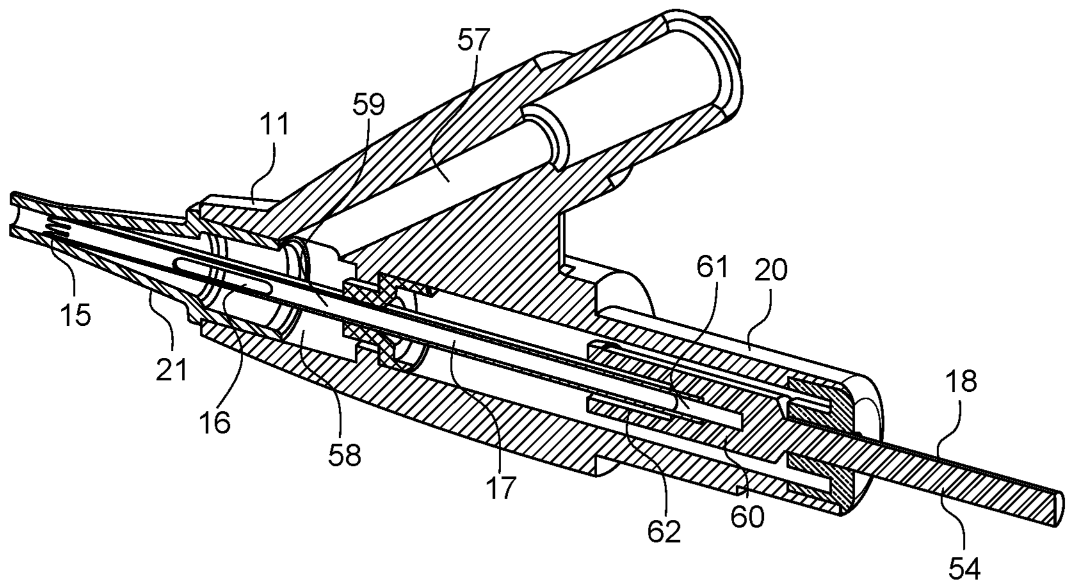
FIG. 9 is a cut-away perspective view of an illustrative needle tubing assembly assembled into a housing.

FIG. 9 shows the abrasion needle tubing installed in the cartridge housing 19. As with other embodiments of the cartridge housing 11, the embodiment shown in FIG. 9 may have a surface 20 used for retention in the mating handpiece and a taper shaped tip 21 that would center and allow the clinician to control the position and location of the needles during abrasion. Embodiments device comprising a tapered tip 14, 21 may help the clinician to be able to preset the protrusion of the needles beyond the end of the tip prior to starting an abrasion procedure to determine depth of needle tip penetration during the abrasion process. Teprsol® or other fluids that assist with dermal abrasion may flow into the housing 11 through an upward angular extending feature 56 with a central bore 57. The fluid may then pass through a cavity 58 in the housing 11 and into the hollow body 59 of the needle tubing through slot 16. The stem 18 may comprise a distal section 60 having a bore 61 formed therein to accommodate a proximal end 62 of the needle tubing 17.

Embodiments of the present invention may comprise: a needle bundle that can be arranged in a circular pattern of tangentially arranged needles that is essentially hollow in the middle; a needle bundle that can be assembled onto a mandrel or created as an assembly and attached to the stem; a needle bundle that can be made with various quantities of needles thereby allowing simpler patterns of manipulation to create the same abrasion result that is desired by the clinician; a needle bundle that can be made stiffer or more flexible depending upon the desire of the clinician for the abrasion process; or a needle bundle that can be assembled into a single use disposable cartridge that can be used for abrading tissue in a shorter amount of clinician time.

Figure 10:
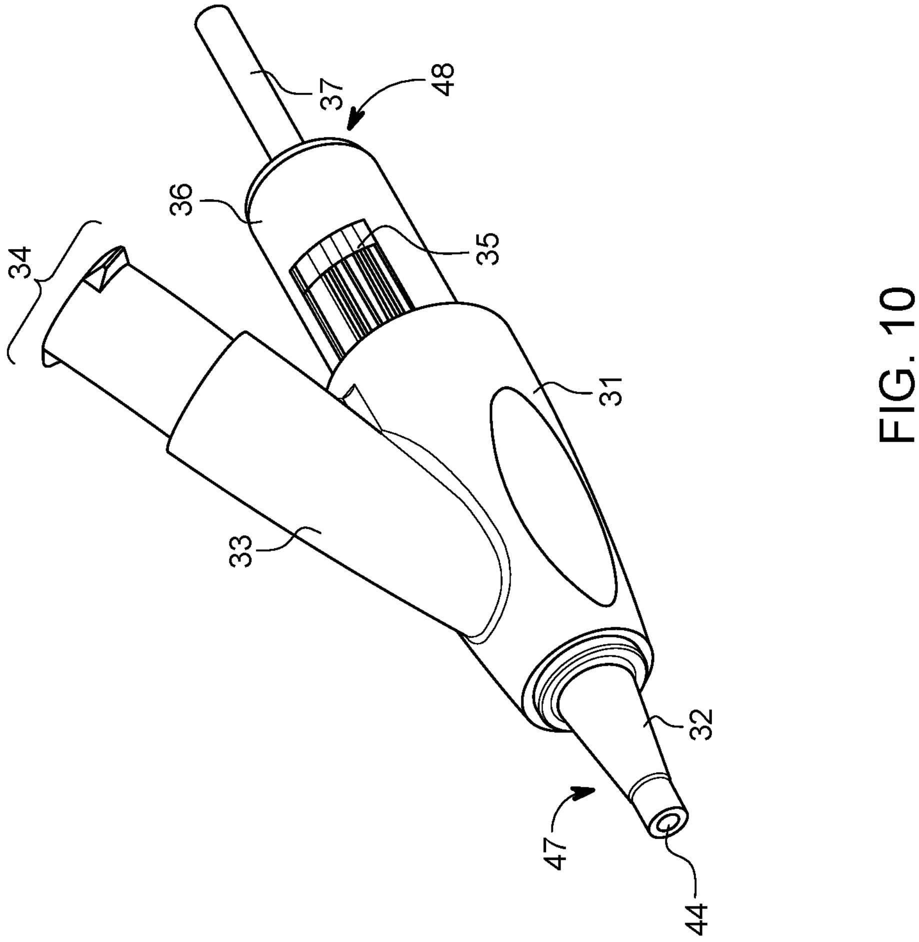
FIG. 10 is a front perspective view of a cartridge in accordance with embodiments of the device.

FIG. 10 shows a frontal view of an embodiment of the device, which may comprise a housing 31 with the upward angular extending feature 33, which houses a bore that extends from the Luer lock interface 34 down to the central bore in the housing 31. The housing 31 may be formed in a single piece. On the distal end 47 of the housing 31 is attached a conical tip 32 that tapers from the outer diameter of the housing down to a smaller diameter containing an aperture 44 through which the sharpened needles 43 (FIG. 13) may pass. The main housing 31 may be fabricated of an injection moldable plastic such as polycarbonate or other appropriate material. The durable nature of this material may provide an advantage in allowing the Luer locking features to retain their strength during use and maintain that strength while in an inventory situation awaiting use.

The housing 31 may further comprise a cylindrical body, extension, or feature 36 extending from the proximal end 48 adapted to aid in positioning the device into a handpiece for use. The cylindrical body 36 may comprise one or more tapered ramps 35 aligned with the central axis of the housing. These ramps 35 may be positioned on the cylindrical body 36 opposite one another. These ramps 35 may be adapted to engage a feature within the handpiece, such that they will interfere with the handpiece feature and the fiction that is caused by this interference will retain the device within the handpiece for use. Thus, the installation of this device into a handpiece may comprise insertion of the cylindrical feature into the handpiece and rotating the device until it is retained.

An actuator rod, shaft, or other feature 37 may extend from the cylindrical body 36 on the housing 31. The rod 37 may directly connect to the needle group within the center of the housing. The rod 37 may interface with the reciprocating features within the handpiece and allow the needles to be driven by the handpiece in a reciprocating action when inserted and locked in place.

Figure 11:
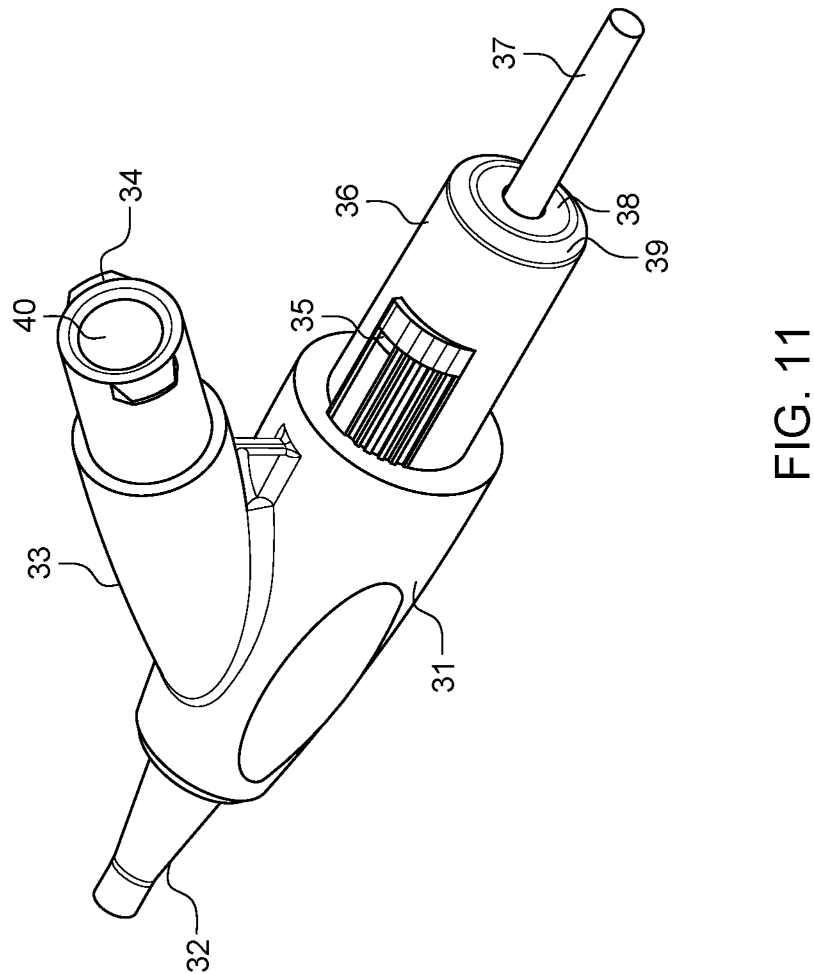
FIG. 11 is a rear perspective view of a cartridge in accordance with embodiments of the device of FIG. 10.

FIG. 11 shows a rearward view of embodiments of the device, showing the housing 31 and the angular feature 33 protruding upward with the Luer locking feature 34 on the end. In the center of the Luer locking feature 34 is an aperture 40 that transmits fluid into the central bore of the housing 31. The cylindrical body 36 protrudes from the end of the housing 31, comprising tapered ramps 35 that are positioned to lock the device in place on a handpiece. Extending from the cylindrical extension 36 of the housing, actuator rod 37 may be attached directly to the needle bundle located within the housing. Surrounding the actuator rod 37 may be a bushing 38 that retains an edge of a combination spring/seal 39 that overlaps with an edge of the cylindrical body 36 of the housing 31. The tapered tip 32 may support the needles during the abrasion process.

FIG. 12 shows various views of the device described above with respect to FIGS. 10-11.

Figure 13:
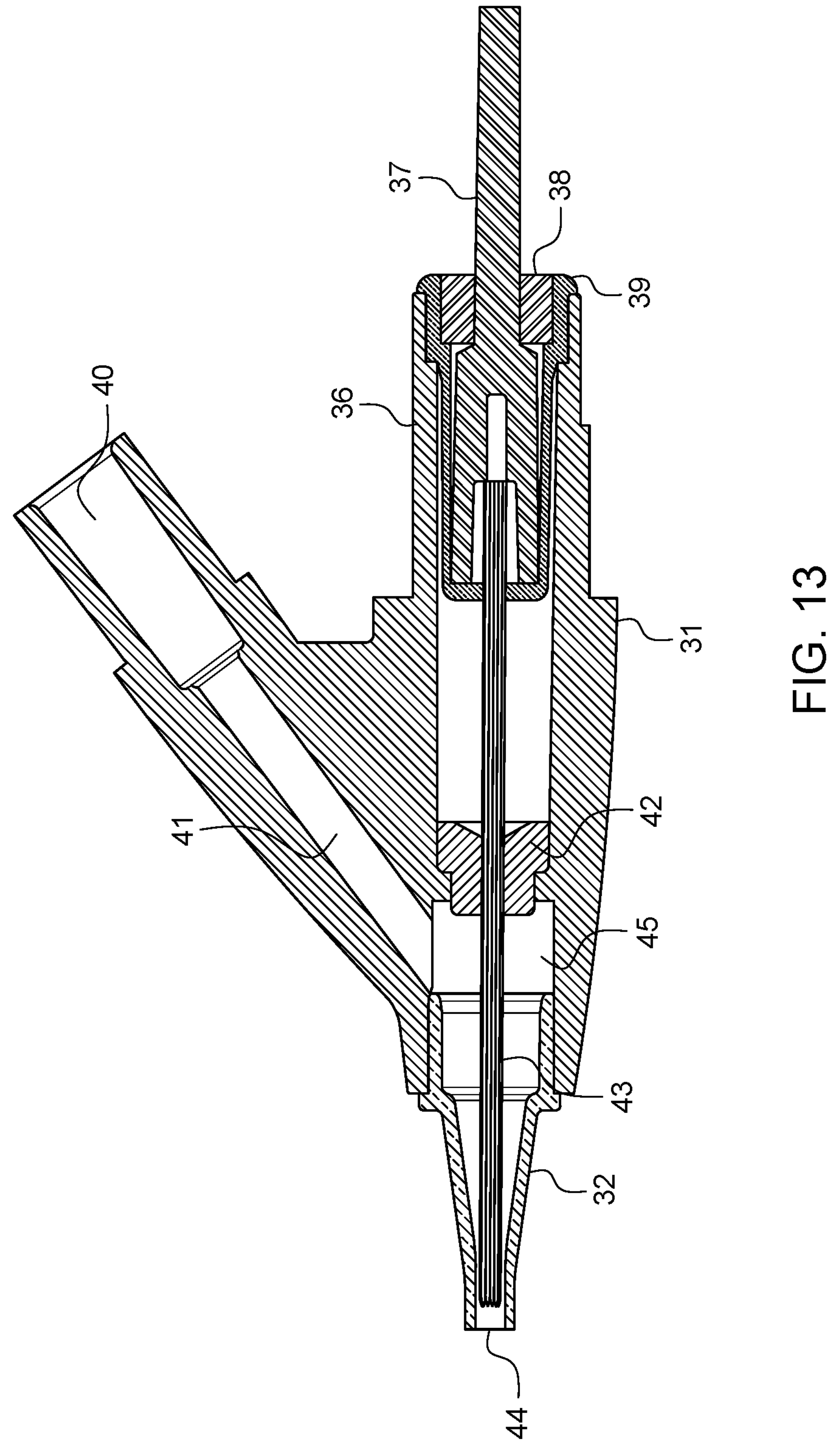
FIG. 13 is a cross-sectional view of a cartridge in accordance with embodiments of the device of FIG. 10.

FIG. 13 shows a sectional view of embodiments of the device such that internal features and components and their relationships to one another can be illustrated. The sectional view illustrates embodiments of the main housing 31, the conical tip 32, and the cylindrical body 36 on the proximal end of the housing 31. The main housing 31 comprises an aperture 40 that it is tapered to a Luer taper, including preferably a taper of 6%. The aperture 40 is connected to a chamber 45 in the main body. The chamber is open to the back side of the conical tip 32 all the way to the aperture 44 on the conical tip. This set of passages allows the Teprsol® to flow from the inlet aperture 40 to the conical tip aperture 44. The needle bundle 43 is attached to the actuator rod 37.

If the actuator rod 37 is operated in a linear reciprocating motion, the needles in the bundle 43 will move in that same linear motion. There may be a bushing 42 that may assist in keeping the needles in alignment during the linear reciprocating motion when rod 37 is moved. If the diameter of the needle bundle is changed or the count of needles is increased from seven, the inner bore of this bushing 42 will be increased as would the aperture 44 of the conical tip 32. The needles may also be kept in alignment with the aperture 44 in the conical tip. The bushing 42 may prevent a portion of Teprsol® fluid from traveling toward the location of the actuator rod 37.

To prevent any fluid that passes bushing 42 from exiting a rear opening of the housing, a combination seal/spring/retainer 39 may be positioned in a rearward end of the cylindrical body 36 of the housing 31. This seal, retainer and spring combination 39 may act as a return spring to help the needles return to their original position during the reciprocating motion caused by the handpiece acting on actuator rod 37. This seal/spring/retainer 39 may comprise a flexible elastomeric material, such as a TPE (thermoplastic elastomer) or a rubber compound such as silicone or biocompatible rubber. Elastomeric properties of the seal/spring/retainer 39 may allow the seal/spring/retainer 39 to stretch and rebound to its original shape to provide a spring action. Since it is sealed to the edges of the inside bore of the cylindrical body 36, the seal/spring/retainer 39 may also prevent the fluid escaping from around the edges.

The combination seal/spring/retainer 39, holds the actuator rod 37 and needle bundle 43 assembly within the housing 31. The combination spring, seal and retainer may be held in place by a circular retainer bushing 38, which may have a small barb feature around is periphery. Once pressed in place, seal/spring/retainer 39 will be retained. The center of the seal/spring/retainer 39 may be small enough in diameter that the inside will presses against the outer diameter of the actuator rod 37 thus sealing it from fluid passing between the needles 43 and the outer edge of the actuator rod 37. This sealing action may provide an advantage of reducing or preventing the discharge of Teprsol® into the inner workings of the handpiece since Teprsol® is corrosive to metal components.

Embodiments of the device may comprise a variety of features or elements, including one or more of: an angular connecting port that connects to the main chamber to deliver fluid to the needle tips; a Luer locking feature on this connecting port; a seal/spring/retainer combination part that provides a positive fluid seal, a return spring and it also retains the components within the housing; an ability to modify the quantity of needles or change the needle pattern by varying the diameter of the conical tip aperture and the guide bushing; or a safety feature of reduced chance of needle pricks with the spring/seal/retainer combination part retracting the needle bundle tips within the conical tip.

What is claimed is:

1. A cartridge for use in dermal abrasion for application and removal of tattoos and other skin treatments, the cartridge comprising:

a housing comprising a proximal end, a distal end, and a cavity; and a needle bundle comprising a central arbor and a plurality of needles, each of the plurality of needles having a sharpened distal end and a non-sharpened proximal end attached to the central arbor; and a stem attached to the needle bundle and extending in a proximal direction from the central arbor and having a distal end and a proximal end;

wherein each of the plurality of needles is arranged adjacent to at least one other of the plurality of needles such that the sharpened distal end of each of the plurality of needles extends beyond the central arbor and the plurality of needles form a hollow circular pattern surrounding the central arbor.

2. The cartridge of claim 1, wherein each of the plurality of needles tangentially abuts an adjacent needle of the plurality of needles.

3. The cartridge of claim 1, wherein the needle bundle further comprises a sleeve surrounding the plurality of needles and securing the plurality of needles to the central arbor.

4. The cartridge of claim 1, wherein the needle bundle further comprises a tube surrounding the plurality of needles and securing the plurality of needles to the central arbor.

5. The cartridge of claim 4, wherein the tube is secured to the proximal end of the plurality of needles by an adhesive.

6. The cartridge of claim 1, wherein the needle bundle further comprises a ring surrounding the plurality of needles and securing the plurality of needles to the central arbor.

7. The cartridge of claim 6, wherein the ring comprises a metal ring.

8. The cartridge of claim 6, wherein the ring comprises a shrink ring.

9. The cartridge of claim 1, wherein the distal end of the stem comprises a mating hole into which the needle bundle is inserted.

10. The cartridge of claim 1, wherein the central arbor comprises a wire.

11. The cartridge of claim 1 further comprising a tapered tip formed adjacent the cartridge distal end, wherein at least a portion of the sharpened distal end of each of the plurality of needles protrudes beyond the tapered tip.

12. A cartridge for use in dermal abrasion for application and removal of tattoos and other skin treatments, the cartridge comprising:

a housing comprising a proximal end, a distal end, and a cavity; and a plurality of needles, each of the plurality of needles having a sharpened distal end and a non-sharpened proximal end; and a stem comprising a distal end and a proximal end, the stem further comprising a central pin extending in a distal direction from the stem;

wherein the plurality of needles is arranged adjacent to one another such that the sharpened distal end of each of the plurality of needles extends beyond the central pin and the plurality of needles form a hollow circular pattern surrounding the central pin.

13. The cartridge of claim 12, wherein the cartridge further comprises an elastomeric retainer providing a biasing force in a direction to retract the plurality of needles into the housing.

14. The cartridge of claim 12, wherein the stem comprises a driving rod that interfaces with a handpiece containing a reciprocating drive.

15. The cartridge of claim 12, wherein the plurality of needles comprises 9 needles.

16. The cartridge of claim 12, wherein the plurality of needles comprises between 7 and 22 needles.

* * * * *